United States Patent [19]

Tamhankar et al.

[11] Patent Number: 5,417,742
[45] Date of Patent: May 23, 1995

[54] REMOVAL OF PERFLUOROCARBONS FROM GAS STREAMS

[75] Inventors: Satish S. Tamhankar, Scotch Plains; Ramakrishnan Ramachandran, Allendale; Martin Bülow, Basking Ridge; Theodore R. Galica, Glen Gardner, all of N.J.

[73] Assignee: The BOC Group, Inc., New Providence, N.J.

[21] Appl. No.: 160,999

[22] Filed: Dec. 3, 1993

[51] Int. Cl.$^6$ .................................... B01D 53/047
[52] U.S. Cl. ............................... 95/96; 95/99; 95/131; 95/143; 95/902; 95/903
[58] Field of Search ............... 95/131, 143–148, 95/902, 903, 96–107, 114, 115

[56] References Cited

U.S. PATENT DOCUMENTS

| | | | |
|---|---|---|---|
| 3,224,167 | 12/1965 | Jones | 95/902 X |
| 3,732,326 | 5/1973 | Chen | 95/143 X |
| 4,102,647 | 7/1978 | Roelse et al. | 95/143 X |
| 4,309,281 | 1/1982 | Dessau | 95/143 X |
| 4,455,444 | 6/1984 | Kulprathipanja et al. | 95/143 X |
| 4,455,445 | 6/1984 | Neuzil et al. | 95/143 X |
| 4,715,965 | 12/1987 | Sigerson et al. | 95/143 X |
| 4,732,584 | 3/1988 | Coe et al. | 55/66 |
| 4,820,318 | 4/1989 | Chang et al. | 95/903 X |
| 4,943,304 | 7/1990 | Coe et al. | 55/66 |
| 5,231,980 | 8/1993 | Filipovic et al. | 128/205.12 |
| 5,261,948 | 11/1993 | Foley et al. | 95/903 X |
| 5,294,246 | 3/1994 | Gardner, Sr. | 95/143 X |
| 5,300,468 | 4/1994 | Senum et al. | 95/148 X |

FOREIGN PATENT DOCUMENTS

| | | | |
|---|---|---|---|
| 3917389 | 12/1989 | Germany | 95/143 |
| 3-108392 | 5/1992 | Japan . | |

OTHER PUBLICATIONS

Silagadze, J. D. et al. "*Microcalorimetric Study of CF4 Adsorption on L & ZSM-5 Type Zeolites*" Bulletin of the Acedemy of Sciences of the Georgian, SSR, 123, No. 2 1986, pp. 317–320.

Primary Examiner—Robert H. Spitzer
Attorney, Agent, or Firm—Coleman R. Reap; Larry R. Cassett

[57] ABSTRACT

Perfluorocarbons are recovered from gas streams by subjecting the gas stream to an adsorption process in a bed of one or more energetically homogeneous adsorbents such as silicon-rich adsorbents of the FAU structure, silicon-rich adsorbents of the BEA structure, silicon-rich adsorbents of the MOR structure. The adsorption process is preferably pressure swing adsorption or temperature swing adsorption.

25 Claims, 2 Drawing Sheets

REMOVAL OF PERFLUOROCARBONS FROM GAS STREAMS

FIELD OF THE INVENTION

This invention relates to the purification of gas streams, and more particularly to the removal of perfluorinated hydrocarbons from gas streams by adsorption.

BACKGROUND OF THE INVENTION

Fully fluorinated hydrocarbon derivatives (perfluorocarbons) are used worldwide in a variety of domestic and industrial applications. As a consequence of such use gaseous perfluorinated hydrocarbons are currently being released to the environment. As an example, low molecular weight perfluorocarbons are used in combination with oxygen in the semiconductor manufacturing industry for silicon chip etching and for cleaning chemical vapor deposition chambers. These processes are typically conducted under vacuum. The exhaust gas from the chamber contains, in addition to the perfluorocarbons, unreacted deposition compounds and a variety of reaction products, such as hydrogen fluoride, nitrogen trifluoride, etc. Since these compounds cannot be safely released to the atmosphere the exhaust gas is generally treated to destroy the potentially harmful compounds or convert them to compounds that can be released to the atmosphere. According to one procedure, the gas stream is introduced into a reactor such as the gas reactor column manufactured by Edwards High Vacuum International Division of The BOC Group, plc under the trade designation EDWARDS GRC, wherein components of the stream are reacted at high temperatures and converted into disposable solid substances. Perfluorocarbons are highly nonreactive, however, and pass through the reactor unaffected. Since perfluorocarbons are nontoxic and are not believed to be harmful to the ozone layer surrounding the earth they are currently discharged to the atmosphere.

Perfluorocarbons are considered global warmers, however, because of their high stability and thermal characteristics. Accordingly, industry worldwide is now making efforts to minimize or discontinue release to the environment of perfluorinated hydrocarbons. Since currently available processes for recovering these compounds from waste gases are costly and not always practical, methods of destroying them have been considered. One proposed method of destruction is combustion. This would be accomplished by heating them to temperatures in excess of 1000° C., which temperatures would be attained by burning hydrogen and oxygen in the presence of the perfluorocarbons.

Destruction of perfluorocarbons is not the best solution to the disposal problem because it is expensive, and incomplete combustion may result in the production of other harmful byproducts. Furthermore, perfluorocarbons are high value products and could be profitably recycled, if they could be recovered from gas streams at reasonable cost. The present invention provides a cost effective and efficient method of accomplishing this objective.

SUMMARY OF THE INVENTION

According to a broad aspect of the invention one or more gaseous perfluorocarbons are separated from a gas stream containing at least one permanent gas by passing the gas stream through one or more of certain energetically homogeneous, silicon-rich, microporous adsorbents and/or one or more of certain energetically homogeneous mesoporous adsorbents. The perfluorocarbons are more strongly adsorbed by these adsorbents than are the other components of the gas stream. The perfluorocarbons are recovered from the adsorbent by conventional regeneration procedures.

The preferred adsorbents are dealuminated type Y zeolite, dealuminated type beta zeolite and dealuminated mordenite, all having a silicon to aluminum ratio of at least 50. The most preferred adsorbent is dealuminated type Y zeolite having a silicon to aluminum ratio of at least 100.

The process of the invention can be used to recover any perfluorocarbons that are gaseous or in vapor form at the adsorption temperature. The invention is especially suitable for the recovery of saturated or ethylenically unsaturated perfluorocarbons, particularly those containing up to 8 carbon atoms, such as perfluoromethane, perfluoroethane, perfluoroethylene, perfluorohexane, perfluorooctane, etc.

The particular adsorption process used is not critical to the invention and, in general, any adsorption procedure can be used. Cyclical adsorption processes are generally employed and pressure swing adsorption (PSA) and temperature swing adsorption (TSA) cycles, or combinations of these, are preferred. The adsorption is preferably carried out in a battery of two or more adsorption beds arranged in parallel and operated out of phase, so that at least one bed is undergoing adsorption while another bed is being regenerated.

In addition to simple adsorption processes, such as described above, the invention can be used to modify certain recycle processes. Specific recycle processes into which the invention can be incorporated include vacuum vapor deposition and etching chamber cleaning processes and perfluoroethylene polymerization processes.

According to the deposition and etching chamber cleaning embodiment a chamber containing deposition or etching chemical deposits is cleaned by introducing a perfluorocarbon and oxygen into the chamber under plasma conditions. The perfluorocarbon and oxygen react with the deposits and form various gaseous products. The gas mixture, comprising reaction products, and unreacted deposition chemicals, perfluorocarbon and oxygen, is removed from the deposition chamber, preferably by evacuation, is optionally diluted with nitrogen or argon and is passed through a reactor at elevated temperatures, thereby converting the deposition chemicals to harmless solids. The perfluorocarbon, which is not converted in the reactor, is removed from the gas reactor column effluent by the above-described adsorption process and is recycled to the deposition or etching chamber or sent to storage for future use. The perfluorocarbon can be subjected to additional purification steps, such as condensation or cryogenic distillation, if it is necessary to increase its purity.

According to the perfluoroethylene polymerization embodiment perfluoroethylene is polymerized in a reactor, thereby producing a product mixture of polymer and unreacted monomer. The unreacted monomer is removed from the product mixture by stripping, preferably with an inert gas. The stripped monomer is then subjected to the above-described adsorption process, thereby adsorbing the perfluoroethylene. After being desorbed from the adsorption bed, the perfluoroethylene is recycled to the polymerization reactor, sent to storage or otherwise disposed of.

DETAILED DESCRIPTION OF THE INVENTION

Figure 1:
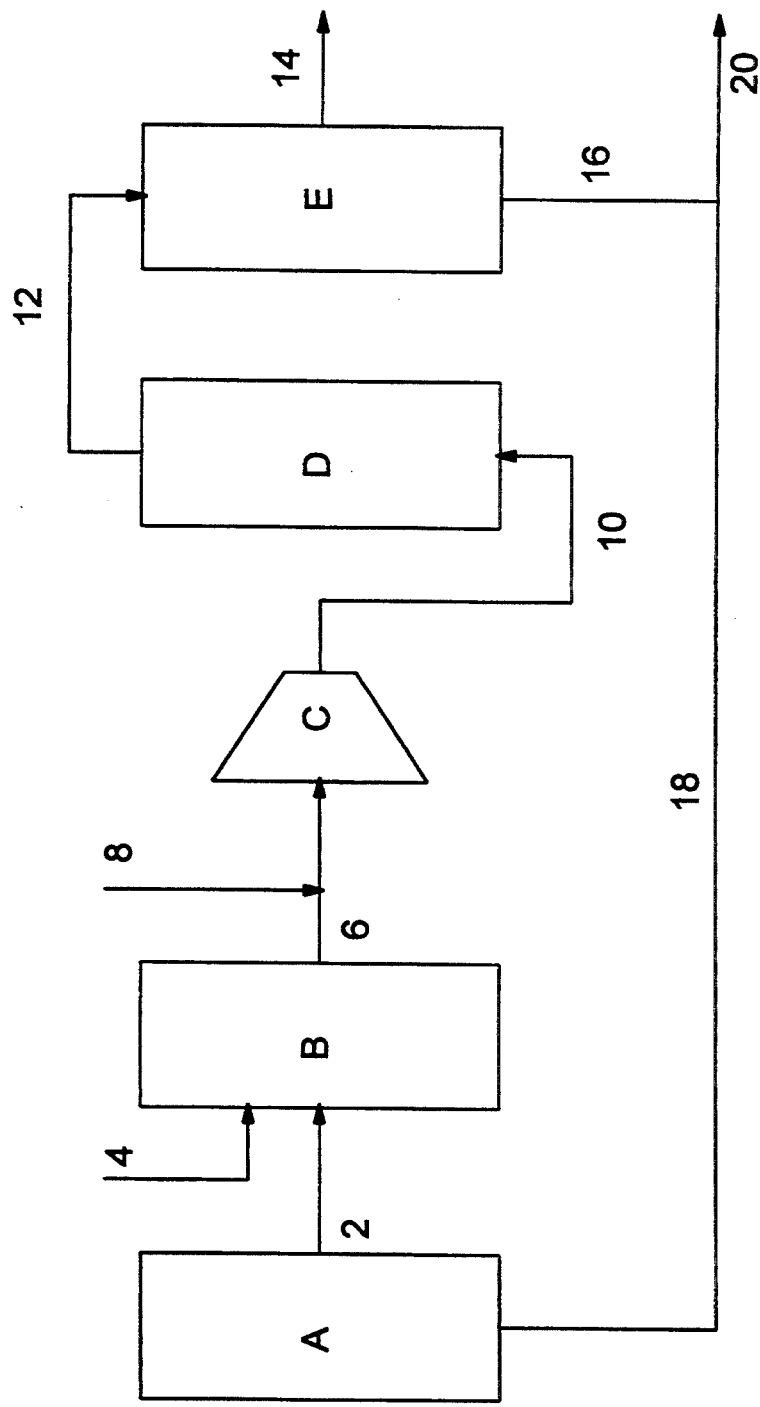
FIG. 1 illustrates, in a block diagram, a specific embodiment of a system for practicing the process of the invention.

Perfluorocarbons are separated from one or more permanent gases by the process of the invention. For purposes of this invention, permanent gases include nitrogen, oxygen, argon, helium, neon, krypton, xenon, hydrogen and carbon monoxide. The invention is particularly suitable for separating perfluorocarbons from nitrogen, oxygen, argon and mixtures of these.

The adsorbents that can be used in the invention include certain energetically homogeneous, microporous and mesoporous substances having pore diameters of at least about 4.5 Angstrom units. For purposes of this description, microporous substances are defined as those having an average pore size of less than about 20 Angstrom units and mesoporous substances are defined as those whose average pore size is in the range of about 20 to about 500 Angstrom units. In an energetically homogeneous adsorbent, the adsorption energies of all adsorption sites are substantially identical. This definition implies that the experimentally measurable heat of adsorption remains substantially constant, even when the concentration of the adsorbed compound(s) varies. "Substantially constant heat of adsorption", as this term is used herein, means that the heat of adsorption of the substance does not vary by more than about 10%.

Suitable microporous adsorbents include silicon-rich modified FAU structure class zeolites, such as dealuminated type Y; silicon-rich modified BEA structure class zeolites, such as dealuminated beta zeolite; and silicon-rich modified MOR structure class zeolites, such as dealuminated mordenite, and carbon molecular sieves (CMS) having pore diameters of at least about 4.5 Angstrom units.

The term "silicon-rich" is here used to mean that the silicon-to-aluminum ratio of the molecular sieve is at least about 50. In the most preferred embodiments the silicon-to-aluminum ratio of the molecular sieve is at least about 100:1. Suitable silicon-rich molecular sieves can be made, for example, by direct synthesis, or by dealuminating molecular sieves of the desired classes. The silicon-rich molecular sieves and the methods of preparing them are well known and their structures and methods of manufacture form no part of the invention.

Suitable mesoporous adsorbents include polymeric carbonaceous adsorbents, such as partially pyrolyzed (carbonized), sulfonated styrene-divinylbenzene copolymers, such as the product sold by Rohm and Haas Company under the trademark Ambersorb ®; and mesoporous silicates of the M41S structure class.

The perfluorocarbons that can be separated by the process of the invention are those that are normally gaseous, i.e. gaseous at ambient temperature and atmospheric pressure, or that are vaporous at the temperature and pressure at which the adsorption step proceeds. The term "perfluorinated hydrocarbon" means aliphatic hydrocarbon derivatives in which all of the hydrogen atoms have been substituted with fluorine atoms. Included in this class of compounds are the saturated and ethylenically unsaturated perfluorocarbons having boiling points up to about 100° C., which includes perfluorocarbons containing up to 8 carbon atoms. Representative examples of perfluorocarbons that can be recovered by the process of the invention are perfluoromethane, perfluoroethane, perfluoropropane, perfluorohexane, perfluorooctane, perfluoroethylene, etc.

For a better understanding of the invention, reference is made to the accompanying drawings, wherein the same reference numerals are used to designate the same or similar pieces of equipment in the figures. Auxiliary equipment not necessary for an understanding of the invention, including compressors, heat exchangers and valves, have been omitted from the drawings to simplify discussion of the invention.

Considering first FIG. 1, A is a perfluorocarbon storage vessel, B represents a vacuum vapor deposition chamber or an etching chamber or a battery of such chambers, C is a vacuum means, D is a reactor and E is an adsorption system. The specific details of the construction and operation of these units are well known, and they form no part of the invention.

Perfluorocarbon and oxygen are fed to chamber B through lines 2 and 4, respectively, and the chamber is evacuated through line 6. Line 6 joins chamber B to the inlet of vacuum means C, which typically is a vacuum pump. On its discharge end, vacuum means C is joined to reactor D through line 10. Reactor D contains one or more agents which react with the components of the gas process stream, and means for heating the gas reaction column to the desired reaction temperature (not shown). The details of gas reactor column D form no part of the present invention and thus are not set forth in this description. On its outlet end, gas reactor column D is joined to unit E by line 12.

Unit E is provided with waste gas discharge line 14 and perfluorocarbon discharge line 16. In the embodiment illustrated in the drawing, line 16 is joined to perfluororcarbon recycle line 18, which serves to return purified perfluorocarbon to vessel A, and to perfluorocarbon discharge line 20.

Various gas treatment units, such as filters or solvent wash scrubbers, may be located in the system between units C and D, between units D and E or in line 14, if desired, to remove particulates and soluble components from the system, but these are not shown since they are not critical to the invention.

The principal purpose of unit E is to separate perfluorocarbons from the gaseous effluent from gas reactor column D. Unit E is typically a pressure swing or temperature swing adsorption system, preferably comprising two or more stationary beds packed with one or more energetically homogeneous molecular sieve adsorbent of the above-described categories. The beds are generally arranged in parallel and adapted to be operated in a cyclic process comprising adsorption and desorption. It is commonplace to have the system in which the adsorption is carried out comprise two or more adsorbent beds cycled out of phase so that one or more adsorbent beds are being operated in the adsorbent phase of the cycle while one or more other adsorption beds are being regenerated.

In practicing the process of the invention illustrated in FIG. 1, perfluorocarbon and oxygen are introduced via lines 2 and 4, respectively, into a chamber of system B in which a chemical deposition or an etching operation has just been completed. The chamber contains various chemical waste deposits which are to be removed from the chamber to prepare it for the next chemical deposition or etching operation. The perfluorocarbon and oxygen contact the waste deposits and react with them to produce gaseous waste products. The gaseous products, together with unreacted perfluorocarbon and oxygen, are withdrawn from the deposition chamber by suction created by vacuum means C. Since the gaseous products and the unreacted oxygen may form a flammable mixture, an inert gas, such as nitrogen, argon or carbon dioxide, is introduced into line 6 through line 8 to prevent premature combustion of the product gas. The gas mixture passing through line 10 is next introduced into reactor D, wherein the mixture is heated to about 600° C. or higher. The various components of the heated mixture contact the reactants in the column and are converted to products that can either be safely discharged to the environment or easily recovered by further chemical treatment. The unreacted perfluorocarbon in line 10 passes through unit D unaffected. The effluent gas from the gas reactor column next enters system E, wherein it is subjected to gas adsorption.

The adsorption process comprises repeating adsorption and bed regeneration steps. In preferred embodiments the adsorption process is pressure swing adsorption, temperature swing adsorption or a combination of the two, the particular adsorption method being determined by the chemical composition of the process gas. The specific conditions under which the adsorption process is carried out determine the efficiency of the adsorption process, but they do not form a part of the invention. These conditions are well known to those familiar with gas adsorption processes and any combination of the widely varying operating conditions used in adsorption processes may be employed in the process of the invention.

In general, the adsorption step is usually carried out at a temperature in the range of about 31 100° C. or lower to about +100° C. and an absolute pressure in the range of about 0.5 to about 20 bar, and is preferably carried out at a temperature in the range of about 15 to about 75° C. and an absolute pressure in the range of about 1 to about 10 bar. The lower the temperature, the better the separation performance of the adsorbent. During the adsorption step of the process, feed gas is introduced into the adsorption system and it flows through each bed that is in the adsorption phase of the cycle. As the gas flows through the bed perfluorocarbon is adsorbed onto the adsorbent. An adsorption front formed at the forward end of the adsorbed perfluorocarbon advances toward the nonadsorbed gas outlet as the adsorption step proceeds. The remainder of the gas stream passes through the bed and leaves system E through line 14 as waste gas. The waste gas may be discharged into the atmosphere, if it is free of components that are harmful to the environment; otherwise, it may be sent to downstream units for further treatment. When the adsorption front reaches the desired point in the adsorption bed, flow of feed gas into the bed is terminated. This marks the end of the adsorption phase of the separation process.

The beds that have just completed the adsorption step next undergo regeneration. The conditions under which bed regeneration is carried out are likewise not critical to the successful practice of the invention. PSA bed regeneration can be carried out at an absolute pressure as low as about 100 millibar or lower, but it is usually carried out at an absolute pressure in the range of about 100 to about 1000 millibar. TSA bed regeneration is carried out by heating the adsorbent to a temperature above the temperature at which the adsorption step is carried out, typically a temperature in the range of about 0° to about 200° C., and preferably to a temperature in the range of about 20° to about 150° C. The desorption may be accomplished by means of heaters and/or by passing steam or a heated inert gas through the bed. During the regeneration step of a TSA cycle the pressure in the adsorption vessel can either remain the same as or be lower than the pressure maintained in the vessel during the adsorption step. It is often preferred to conduct temperature swing processes at or near atmospheric pressure. When combinations of pressure swing adsorption and temperature swing adsorption cycles are employed the temperature is higher and the pressure is lower during the bed regeneration step than they are during the adsorption step of the cycle.

During regeneration, perfluorocarbon is desorbed from unit E through line 16. The recovered perfluorocarbon can be returned to storage vessel A through line 18, if it is of suitable purity to be recycled to the system, or it can be discharged from the system through line 20 for further purification.

Figure 2:
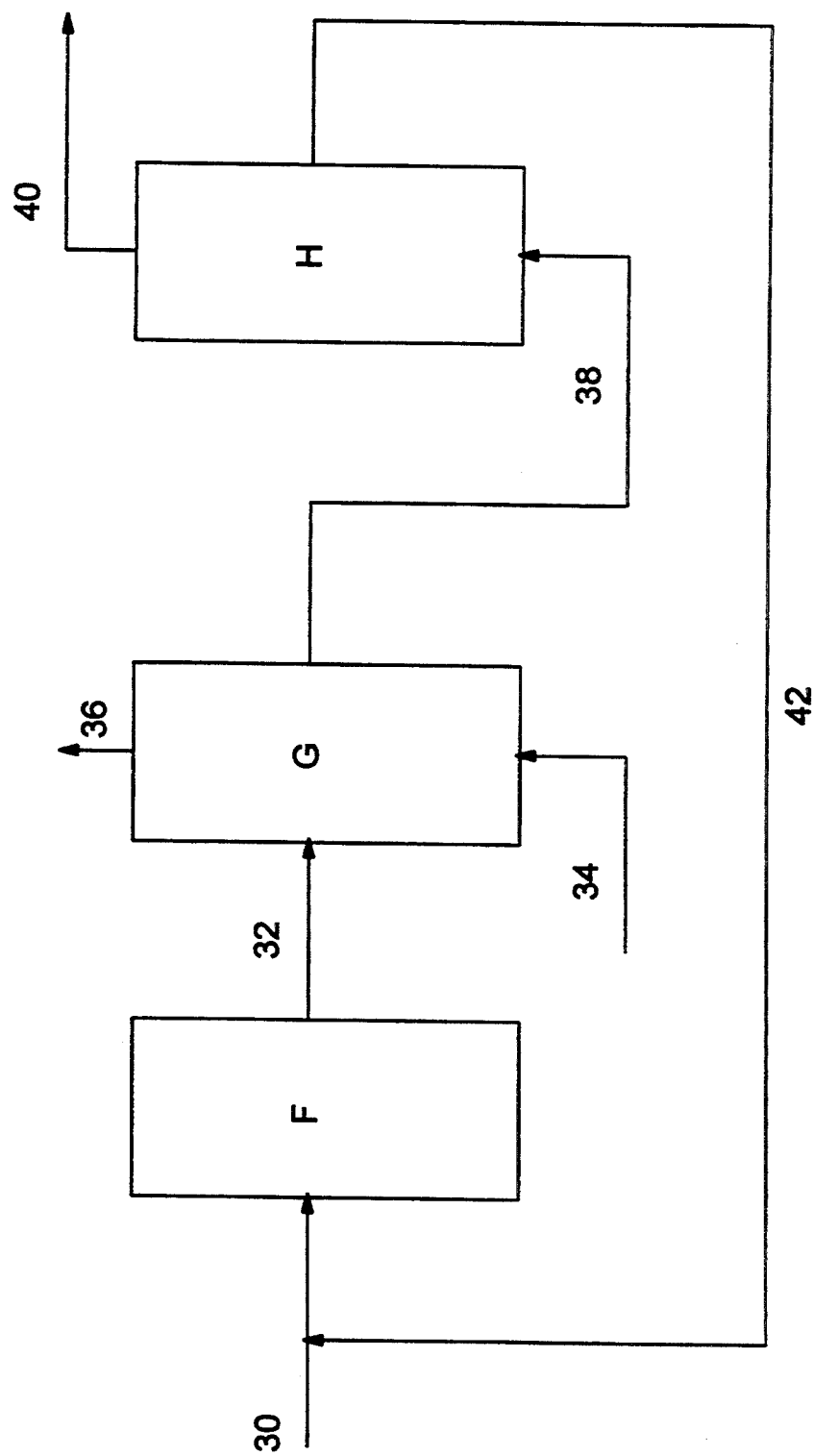
FIG. 2 illustrates, in a block diagram, a second embodiment of the process of the invention.

In the embodiment of the invention illustrated in FIG. 2, F represents a polymerization reactor, G is a polymer recovery unit and H is a tetrafluoroethylene adsorption system. All of these units and systems are well known and the specific details of their construction and operation form no part of this invention.

Reactor F is equipped with monomer feed line 30 and polymer discharge line 32. Reactor F is a typical batch or continuous tetrafluoroethylene polymerization reactor and it is provided with all standard features necessary for the polymerization of the tetrafluoroethylene monomer, such as a catalyst feed line, means for agitating the reactor contents during the polymerization and means for heating the reactor contents, none of which is illustrated.

Polymer discharge line 32 is connected to the inlet of polymer recovery unit G. Unit G is typically a stripping unit and it is provided with stripping gas inlet line 34, polymer recovery line 36 and stripped gas outlet line 38. Line 38 is connected to the inlet of adsorption unit H, which is similar to or identical to unit E of FIG. 1. Unit H is provided with waste gas line 40 and tetrafluoroethylene recycle line 42.

In practicing the invention in the system of FIG. 2, tetrafluoroethylene and other desired additives, such as catalyst and polymer moderating agents, etc. are introduced into reactor F either through line 32 or through separate feed lines. The polymerization may be carried out on a batch or continuous basis, either in the liquid or gaseous phase. A mixture of polymer product and unreacted monomer is removed from reactor F through line 32 and introduced into polymer recovery unit G. In unit G the polymer is stripped with an inert gas, such as nitrogen or argon, thereby stripping unreacted monomer from the polymer. The stripped polymer is removed from unit G through line 36 and sent to further processing units located downstream of the system of FIG. 2, and the stripped gas stream, which contains the stripping gas and unreacted tetrafluoroethylene, is discharged from unit G through line 38 and is introduced into adsorption recovery unit H. In unit H, unreacted tetrafluoroethylene is adsorbed from the feed stream in the manner described above with respect to the system of FIG. 1, The sorbed tetrafluoroethylene is next desorbed from the adsorbent and recycled to reactor F through line 42, if the polymerization process is continuous, or sent to tetrafluoroethylene storage, if the polymerization is of the batch type.

The invention is further illustrated by the following examples in which, unless otherwise indicated, parts, percentages and ratios are on a volume basis.

EXAMPLE 1

A gas chromatographic column ¼ inch in diameter and 2 feet long was packed with 1/16 inch extruded pellets of dealuminated type Y sold by Degussa AG under the trade designation Degussa Wessalith DAY type zeolite. With the column being maintained at a temperature of 0° C. helium, as a carrier gas, was passed therethrough at a flow rate of 30 ml/min. A sample gas mixture made up of nitrogen with 1% tetrafluoromethane ($CF_4$) and 2% hexafluoroethane ($C_2F_6$) was injected into the carrier gas stream and passed through the adsorbent-packed column. The elution times for each of the components is recorded in Table 1. The $CF_4/N_2$ and $C_2F_6/N_2$ separation factors for the runs were determined and they also are recorded in Table 1. The above procedure was repeated at temperatures of 20° and 30° C., and the results of these runs are likewise recorded in Table 1.

TABLE 1

| Run | Adsorption Temp. °C. | Retention Time, min | | | Separation Factor | |
|---|---|---|---|---|---|---|
| | | $N_2$ | $CF_4$ | $C_2F_6$ | $CF_4/N_2$ | $C_2F_6/N_2$ |
| 1 | 0 | 0.67 | 2.96 | — | 4.42 | — |
| 2 | 20 | 0.57 | 2.10 | 15.29 | 3.68 | 26.83 |
| 3 | 30 | 0.52 | 1.58 | 11.06 | 3.07 | 21.48 |

EXAMPLE 2

In this example a series of pressure swing adsorption runs was conducted using as feed various nitrogen-hexafluoroethane ($C_2F_6$) gas mixtures. The feed stream for Runs 1, 2, 3, and 5 comprised nitrogen and $C_2F_6$. The feed stream for Run 4 comprised in addition to nitrogen $C_2F_6$, 4% oxygen. All runs were carried out in a pair of cylindrical adsorption vessel 20 inches long and having a diameter of 1.25 inches. In Runs 1 to 4 the adsorption beds were packed with Degussa Wessalith DAY type zeolite, and in Run 5, the beds were packed with Ambersorb ® 563 adsorbent. The adsorption vessels were operated out of phase with each other using a 30 minute adsorption cycle having as steps—feed pressurization: 3 sec; adsorption: 447 sec; bed equalization, depressurization: 3 sec; bed evacuation: 447 sec; bed equalization, repressurization: 3 sec; product backfill: 3 sec. In runs 1,2 and 5, bed equalization was top-to-top and in runs 3 and 4, equalization was top-to-bottom. The adsorptions were conducted at a pressure of 3.77 bar and at various temperatures and flow rates, as indicated in Table 2. During the evacuation step the adsorption vessel was evacuated by means of a vacuum pump to an absolute pressure of 100 mbar. The adsorption temperatures, feed flow rates in liters per minute (l/min), feed and product gas hexafluoroethane concentration, and percentage $C_2F_6$ recoveries are recorded in Table 2 (Runs 1-4).

TABLE 2

| Run | Adsorption Temp. °C. | Feed Flow l/m | Feed $C_2F_6$ Conc, % | Product $C_2F_6$ Conc, % | $C_2F_6$ Recovery % |
|---|---|---|---|---|---|
| 1 | 25 | 0.3 | 2.21 | 11.74 | 93.99 |
| 2 | 5 | 0.3 | 3.05 | 13.35 | 98.95 |
| 3 | 5 | 0.5 | 9.76 | 49.00 | 87.29 |
| 4 | 25 | 0.25 | 5.09 | 22.93 | 93.39 |
| 5 | 25 | 0.50 | 1.31 | 5.3 | 98.44 |

Although the invention has been described with particular reference to specific examples, the examples are merely representative of the invention and variations are contemplated. For instance, the adsorption bed can comprise a mixture of two or more adsorbents of the above-described types, or two or more of the adsorbents can be used in tandem. Furthermore, the invention can be practiced simply as an adsorption process, as part of a deposition chamber cleaning process or an etching process, or as part of other processes in which it is desired to recover perfluorocarbons. For example, the invention can be used to recover perfluorocarbons formed during aluminum refining operations, or to separate perfluorocarbons from lasing gases, or to recover refrigeration gases. The scope of the invention is limited only by the breadth of the appended claims.

What is claimed is:

1. A process for separating at least one gaseous perfluorinated hydrocarbon from a gas stream containing said perfluorinated hydrocarbon and one or more permanent gases comprising passing said gas stream through an adsorbent selected from silicon-rich adsorbents of the FAU structure, silicon-rich adsorbents of the BEA structure, silicon-rich adsorbents of the MOR structure, carbon molecular sieves having a pore diameter of at least 4.5 Angstrom units, carbonized, sulfonated styrene-divinylbenzene copolymers, mesoporous silicates of the M41S structure class and mixtures of these, thereby adsorbing said at least one perfluorinated hydrocarbon from said gas stream.

2. The process of claim 1, wherein said at least one gaseous perfluorinated hydrocarbon contains 1 to 8 carbon atoms.

3. The process of claim 2, wherein said at least one gaseous perfluorinated hydrocarbon is selected from tetrafluoromethane, hexafluoroethane, octofluoropropane, tetrafluoroethylene and mixtures of these.

4. The process of claim 3, wherein said one or more permanent gases is selected from nitrogen, oxygen, argon and mixtures of these.

5. The process of claim 1, wherein said one or more permanent gases is selected from nitrogen, oxygen, argon and mixtures of these.

6. The process of claim 1, wherein said adsorbent is a silicon-rich adsorbent of the FAU structure.

7. The process of claim 6, wherein said adsorbent is dealuminated type Y zeolite.

8. The process of claim 7, wherein said dealuminated type Y zeolite has a silicon-to-aluminum ratio of at least about 100.

9. A cyclic adsorption process for separating one or more gaseous perfluorocarbons from a nitrogen-containing gas stream comprising the steps; (a) passing said gas stream through at least one bed of adsorbent selected from silicon-rich adsorbents of the FAU structure, silicon-rich adsorbents of the BEA structure, silicon-rich adsorbents of the MOR structure, carbon molecular sieves having a pore diameter of at least 4.5

Angstrom units, carbonized, sulfonated styrene-divinylbenzene copolymers, mesoporous silicates of the M41S structure class and mixtures of these, thereby adsorbing said one or more gaseous perfluorocarbons from said gas stream, and (b) desorbing the adsorbed one or more gaseous perfluorocarbons from said adsorbent.

10. The process of claim 9, wherein said cyclic adsorption process is selected from pressure swing adsorption, temperature swing adsorption and combinations of these.

11. The process of claim 9 wherein the adsorption step of said cyclic adsorption process is conducted at a temperature in the range of about $-100°$ to about $100°$ C. and an absolute pressure in the range of about 0.5 to 20 bar.

12. The process of claim 9, wherein said one or more gaseous perfluorocarbons are selected from tetrafluoromethane, hexafluoroethane, octofluoropropane, tetrafluoroethylene and mixtures of these.

13. The process of claim 12, wherein said adsorbent is dealuminated type Y zeolite.

14. The process of claim 13, wherein said dealuminated type Y zeolite has a silicon-to-aluminum ratio of at least about 100.

15. A process for cleaning a chamber containing silicon vapor treatment chemical residues comprising the steps:
 (a) passing a gaseous perfluorocarbon and oxygen through the chamber, thereby forming a gas mixture containing reaction products, oxygen and unreacted perfluorocarbon;
 (b) introducing into said gas mixture an inert gas selected from nitrogen, argon and mixtures of these;
 (c) passing said gas mixture through a reactor containing chemical compounds that react with said reaction products, thereby substantially removing said reaction products from said gas mixture but not significantly affecting said perfluorocarbon; and
 (d) subjecting the substantially reaction product-free gas mixture to a cyclic adsorption process in at least one bed of adsorbent selected from silicon-rich adsorbents of the FAU structure, silicon-rich adsorbents of the BEA structure, silicon-rich adsorbents of the MOR structure, carbon molecular sieves having a pore diameter of at least 4.5 Angstrom units, carbonized, sulfonated styrenedivinylbenzene copolymers, mesoporous silicates of the M41S structure class and mixtures of these, thereby separating said perfluorocarbon from said substantially reaction product-free gas mixture.

16. The process of claim 15, further comprising recycling the separated perfluorocarbon to said chamber.

17. The process of claim 15, further comprising, prior to step (c), scrubbing said gas mixture with a solvent for at least one reaction product contained in said gas mixture.

18. The process of claim 15, wherein said chamber is a vapor deposition chamber or a silicon chip etching chamber.

19. The process of claim 15, wherein said adsorbent is dealuminated type Y zeolite.

20. The process of claim 18, wherein said dealuminated type Y zeolite has a silicon-to-aluminum ratio of at least about 100.

21. A process for polymerizing tetrafluoroethylene comprising the steps:
 (a) contacting tetrafluoroethylene with a catalyst in a polymerization reactor, thereby forming a product mixture comprising polytetrafluoroethylene and unreacted tetrafluoroethylene;
 (b) stripping said product mixture with an inert gas, thereby forming a stripped gas mixture comprised of stripping gas and unreacted tetrafluoroethylene therefrom; and
 (c) subjecting said stripped gas mixture to a cyclic adsorption process in at least one bed of adsorbent selected from silicon-rich adsorbents of the FAU structure, silicon-rich adsorbents of the BEA structure, silicon-rich adsorbents of the MOR structure, carbon molecular sieves having a pore diameter of at least 4.5 Angstrom units, carbonized, sulfonated styrene-divinylbenzene copolymers, mesoporous silicates of the M41S structure class and mixtures of these, thereby separating unreacted tetrafluoroethylene from said stripped gas mixture.

22. The process of claim 21, further comprising recycling unreacted tetrafluoroethylene from step (c) to said polymerization reactor.

23. The process of claim 21, wherein said adsorbent is dealuminated type Y zeolite.

24. The process of claim 23, wherein said dealuminated type Y zeolite has a silicon-to-aluminum ratio of at least about 100.

25. The process of claim 21, wherein said inert gas is selected from nitrogen, argon and mixtures of these.

* * * * *